(12) United States Patent
Dimmit et al.

(10) Patent No.: US 8,093,438 B2
(45) Date of Patent: Jan. 10, 2012

(54) PROCESS FOR PRODUCING 1,1 DIARYL ALKANES AND DERIVATIVES THEREOF

(75) Inventors: Jeffrey Howard Dimmit, Joplin, MO (US); Mike Douglas Cagle, Riverton, KS (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/987,200

(22) Filed: Jan. 10, 2011

(65) Prior Publication Data

US 2011/0172481 A1    Jul. 14, 2011

Related U.S. Application Data

(60) Provisional application No. 61/294,187, filed on Jan. 12, 2010.

(51) Int. Cl.
*C07C 1/207* (2006.01)
(52) U.S. Cl. ...................................... 585/469
(58) Field of Classification Search .................... 585/469
See application file for complete search history.

(56) References Cited

U.S. PATENT DOCUMENTS

| 4,814,537 A | 3/1989 | King |
| 4,895,988 A | 1/1990 | Clerici et al. |
| 6,207,866 B1 | 3/2001 | Kawamata et al. |
| 2003/0013932 A1 | 1/2003 | Okuhara |

FOREIGN PATENT DOCUMENTS

| FR | 2 745 285 | 8/1997 |
| JP | 02-134332 | 5/1990 |

OTHER PUBLICATIONS

H-B. Sun, et al., Tetrahedron Letters, vol. 47, No. 14, pp. 2291-2294 (2006).

*Primary Examiner* — Thuan Dinh Dang
(74) *Attorney, Agent, or Firm* — Oblon, Spivak, McClelland, Maier & Neustadt, L.L.P.

(57) ABSTRACT

A process of producing a 1,1-diaryl alkane comprising a condensation reaction of an aromatic compound having at least one aromatic hydrogen with an acetal, in the presence of a perfluorinated sulfonic acid in polymeric form as catalyst.

7 Claims, No Drawings

PROCESS FOR PRODUCING 1,1 DIARYL ALKANES AND DERIVATIVES THEREOF

BACKGROUND OF THE INVENTION

1. Field of the Invention

The present invention relates to a process for producing 1,1-diaryl alkanes by condensation of aromatic compounds with acetals using a perfluorinated sulfonic acid in polymeric form as catalyst.

2. Description of the Background

Methods of producing diaryl alkanes are known in the art.

JP 02-134332 A discloses a process for producing diaryl methanes which comprises reacting aromatic hydrocarbons and formaldehyde in the presence of a sulfuric acid catalyst and in the presence of surfactants.

FR 2745285 A1 discloses the C-alkylation of aromatic compounds using a particular catalyst, which catalyst comprises a rare earth on a clay, silica and/or alumina support.

U.S. Pat. No. 4,814,537 A discloses a process for preparing methyl-substituted diphenyl methanes by coupling methyl-substituted benzene by contacting with a solid heterogeneous catalytic oxide of vanadium, molybdenum, rhenium and/or tungsten.

U.S. Pat. No. 4,895,988 A discloses the condensation of aromatic compounds with carbonyl compounds, such as phenol(s) with formaldehyde, catalyzed by specific zeolite(s), to produce diaryl alkanes.

US 2003/0013932 A1 discloses a process for producing diaryl methanes and their derivatives, using a methylenating agent such as formaldehyde in the presence of a heteropolyacid catalyst.

Tetrahedron Letters (2006) 47 (14), 2291-2294 discloses the synthesis of diaryl methanes via $InCl_3$-$4H_2O$-catalyzed dehydration of electron-rich arenes with trioxane.

U.S. Pat. No. 6,207,866 discloses a process for producing diaryl methane or its derivatives by reacting dimethoxymethane (DMM) and an aromatic compound at a reaction temperature in the range of 80 to 400° C. in the presence of an acid catalyst. The patent discloses further that the DMM may be prepared by the reaction of an alcohol and formaldehyde in the presence of an acid catalyst.

The issue with the above mentioned prior art is that the reported isomer selectivity when the reaction involves substituted aromatic compounds such as xylene, is poor. In addition, the reaction yields are not acceptable. Above-referenced U.S. Pat. No. 6,207,866 lists acidic cation exchange resins such as sulfonated styrene-divinyl benzene copolymer and sulfonated perfluoroethylene copolymer under the trade name Nafion® in the preparation of above-discussed DMM from an alcohol and formaldehyde.

SUMMARY OF THE INVENTION

The present invention is directed to a process for preparation of 1,1-diaryl alkanes by the condensation of aromatic compounds with acetals using a perfluorinated sulfonic acid in polymeric form as catalyst. Applicants have found that this catalyst allows the reaction to produce 1,1-diaryl alkanes in high yield and with improved isomeric selectivity.

DETAILED DESCRIPTION OF THE INVENTION

An embodiment of the present invention is a process for preparation of 1,1-diaryl alkanes by the condensation of aromatic compounds with acetals using a perfluorinated sulfonic acid in polymeric form as catalyst.

The aromatic compound used as a starting material is not particularly limited. However, it must have at least one aromatic hydrogen and be able to enter into a condensation reaction with the acetal. Useful aromatic compounds include carbocyclic compounds having the structure (1)

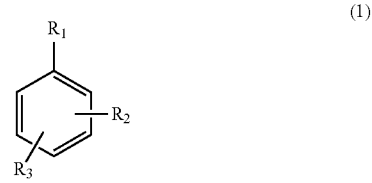

(1)

where $R_1$ is hydrogen or an alkyl group having from 1 to 4, preferably from 1 to 2 carbon atoms, $R_2$ and $R_3$ are independently hydrogen or an alkyl group having from 1 to 4, preferably from 1 to 2 carbon atoms and $R_1$ and $R_2$ may form together a carboxylic ring system which can be saturated or unsaturated.

Examples of the former are benzene, toluene, m-, o-, and p-xylene, cumene, ethylbenzene, pseudocumene, naphthalene, and the like. A preferred aromatic compound is o-xylene.

The acetal is not particularly limited provided it can enter into a condensation reaction with the aromatic compound. Useful acetals include compounds having a structure (2)

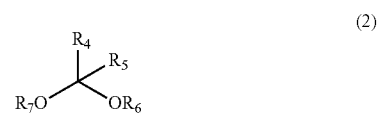

(2)

where $R_4$ and $R_5$ are each independently hydrogen, an alkyl group having from 1 to 6 carbon atoms, preferably hydrogen or an alkyl group having from 1 to 2 carbon atoms, more preferably hydrogen, $R_6$ and $R_7$ are each independently an alkyl group having from 1 to 6 carbon atoms, preferably from 1 to 2 carbon atoms.

Preferred acetals are those derived or derivable from the reaction of formaldehyde or an aldehyde containing 1 to 6 carbon atoms, and methanol. A preferred acetal is DMM.

Catalysts which are used in the process according to the invention are perfluorinated sulfonic acid in polymeric form. Preferably, catalysts are used which are solid supported protic acids and particularly supported perfluorinated sulfonic type of acids in a polymeric form with silica as support material. Such catalysts are available under the trade name Nafion®, Aciplex® F, Femion®, Neosepta®, Fumion® F, and others. A preferred catalyst is Nafion® SAC-13. Nafion® SAC-13 is a porous silica particle that has had Nafion® absorbed onto it at about a 13 wt % loading.

The perfluorinated sulfonic acid in polymeric form has preferably the following structure:

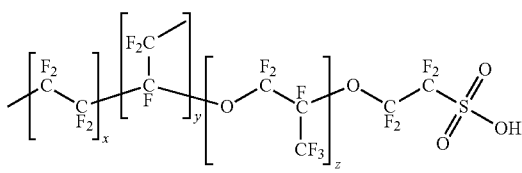

The advantage of using a perfluorinated sulfonic acid in polymeric form as catalyst in this process according to the invention is that the 1,1-diaryl alkane can be produced with higher molar yield and more importantly with higher isomeric selectivity than in a process using catalysts according to the prior art. The molar yield and the isomeric selectivity can be increased by using a solid or supported perfluorinated sulfonic acid in polymeric form as catalyst. Further these solid or support acids have the advantage that there is less fouling and no secondary separation is required.

The aromatic compound can serve as both the solvent and the reactant. Therefore in the process according to the invention the ratio of the acetal to the aromatic compound is preferably from 0.04 to 25% by weight, particularly preferably from 4 to 10% by weight and most preferably from 5 to 8% by weight based on the aromatic compound. If the loading of the acetal in the aromatic compound is increased much above the mentioned ratio, there is an increase in the polymer formation (yield loss and fouling of the catalyst). This ratio is a good balance between yield and through put/productivity.

The acetal can be either premixed with the aromatic compound or fed separately into the process. Preferably the acetal is premixed with the aromatic compound and subsequently fed in the reactor.

A further solvent in addition to the aromatic compound is not necessarily used in the process according to this invention. This has the advantage that an additional purification is not required and that the risk of undesirable interaction is lower.

The reaction can be carried out in a batch reaction, a continuous stirred tank reactor, a catalyst bed reactor, or a packed column. Preferably the reaction is carried out in a catalyst bed reactor, or in a packed column since the catalyst will need to be exchanged at some point and it is desirable to minimize the handling of the material. Using a continuous process the space velocity is preferably in the range from 1 to 4 $h^{-1}$, more preferably from 1.5 to 3.5 $h^{-1}$. According to this invention the definition of space velocity is grams of reaction mixture per hour/grams of catalyst used.

The process may be carried out at a temperature range of 20°-250° C., preferably 110°-220° C., more preferably 160°-180° C.

The process can be run at ambient or under pressure. It is preferred to operate under a pressure from 1000 to 2000 kPa, more preferred from 1250 to 1500 kPa, to ensure a single reaction phase in the reactor.

In a preferred practice of the process, a tubular reactor is packed with a solid-supported perfluorosulfonic acid resin, which is heated to the desired temperature, such as 110°-220° C. A mixture of DMM, such as in an amount of 0.04-25 wt %, in o-xylene is pumped into the tubular reactor containing the catalyst at a space velocity of 0.01-200 $hr^{-1}$. The process can be run at ambient or under pressure. It is preferred to operate under a pressure from 1250 to 1500 kPa, to ensure a single reaction phase in the reactor.

The reaction product can be worked up by distillation, preferably by fractional distillation. The excess of the aromatic compound removed from the reaction mixture can be used in a further process.

Higher isomeric purity of the 1,1-diaryl alkane can be obtained by fractional crystallization or zone refining.

EXAMPLES

The present invention will be described in more detail with reference to various examples. However, there is no intent to limit the embodiments of the invention to the examples.

Example 1

A tubular reactor (2.54 cm×38.1 cm stainless steel) was charged with 18.01 grams of a solid-supported perfluorosulfonic acid resin (Nafion® SAC-13). The catalyst bed was dried by heating to 150° C. with a nitrogen purge overnight. The packed reactor was cooled to ambient temperature and a back pressure regulator, set to 1379 kPa, was attached to the exit of the reactor. The system was primed with o-xylene at 0.89 ml/min flow and the reactor bed was heated to 170° C. Once the reactor bed was at temperature, the pure o-xylene feed was replaced with a solution of 6% by weight DMM in o-xylene and the flow rate was maintained at 0.89 ml/min. Analysis of the product stream exiting the tubular reactor indicated that the dixylyl methane (DXM) was produced with a 79 mol % yield, and with a selectivity of about 75% for the isomer 3,3',4,4'-tetramethyldiphenyl methane.

Example 2

DXM synthesis from DMM and o-xylene using a solid-supported perfluorosulfonic acid resin (Nafion® SAC-13) was carried out using an equipment setup similar to that described in Example 1.

The catalyst filled tube reactor was prepared-by heating at 150° C. overnight with a nitrogen purge. The tube reactor was allowed to cool to room temperature. The pump was turned on and the DMM/o-xylene mixture flow was established at 1.0 ml/min. The tube furnace temperature was set to 40° C. and the reactor temperature was increased by 15° C. every 0.5 to 2.0 hours. The molar yield of DXM was observed to increase with temperature up to 140° C. DMM was detected in the product stream until a reaction temperature reached 180° C. The best molar yield (85%), selectivity (70 to 75%) and DMM conversion (100%) occurred at 180° C. for a space velocity of 2.9 $hr^{-1}$ (1.0 ml/min) and a 6% by weight DMM concentration.

Example 3

DXM synthesis from DMM and o-xylene using a perfluorosulfonic acid resin was carried out using an equipment setup similar to that described in Example 1.

The catalyst filled tube reactor was prepared-by heating at 150° C. overnight with a nitrogen purge. The tube reactor was allowed to cool to room temperature. The pump was turned on and the DMM/o-xylene mixture flow was established at 1.0 ml/min. The tube furnace temperature was set to 40° C. and the reactor temperature was increased until the reaction temperature reached 160°, 170°, or 180° C. and was then held at that temperature for a period of 8-10 hours while periodically sampling the product stream Analysis demonstrated that the DXM molar yield was constant at 60%. It was also observed that the isomeric selectivity was consistent over this range at 70%.

Comparative Example 1

DXM synthesis from DMM and o-xylene using, a variety of acid catalysts, such as activated weakly acidic alumina oxide, activated neutral alumina oxide, and alumina oxide with 1% $H_3PO_4$ loading, respectively, was carried out using an experimental set up similar to that described in Example 1.

The reactor was heated to 100° C. and a flow of a 6 wt % solution of DMM in o-xylene was established at 1.0 ml/min. Samples were collected every 30 min and the tube furnace temperature was increased by 20° every hour. Gas was observed evolving from the reactor column at temperatures above 140° C. Once the reactor temperature reached 360° C., the reaction was stopped.

DXM was not found to be produced during the evaluation of each of these alternate catalysts. These experiments, however, demonstrate that the upper temperature that can be used with DMM is 180 to 200° C. due to its decomposition. The degradation of the DMM as indicated by GC analysis is shown in Table 1. The similarity of these data indicates that this decomposition is independent of the catalyst.

TABLE 1

| | Content of dimethoxymethane [%] | |
|---|---|---|
| Temperature | activated weakly acidic alumina oxide as catalyst | alumina oxide with 1% $H_3PO_4$ loading as catalyst |
| 25 | 100 | 100 |
| 100 | 90 | 92 |
| 120 | 92 | 95 |
| 140 | 90 | 95 |
| 160 | 86 | 93 |
| 180 | 56 | 84 |
| 200 | 54 | 54 |
| 220 | 38 | 24 |
| 240 | 0 | 0 |

Comparative Example 2

DXM synthesis from DMM and o-xylene using a sulfonic acid resin (Amberlyst® XN 1010-sulfonated styrene-divinyl-benzene-hydrogenform with a high surface area) using an experimental set up similar to that described in Example 1.

Flow to the tube reactor was established at 1.0 ml/min and the furnace temperature was set to 60° C. Samples were collected every 30 min and the temperature was increased by 20° C. every 0.5 to 2.0 hours. The product stream exiting the tube reactor became yellow in color when the reactor was at 110° C. Gas was observed evolving from the reactor column at temperatures above 140° C. and the trial was stopped when the reactor temperature reached 150° C. As can be seen in Table 2, the best result with this catalyst was a molar yield of 39% with a selectivity of 60%. This comparative example indicated that the sulfonic acid resin gives unsatisfactory yields of DXM in a single pass continuous flow system.

Comparative Example 3

DXM synthesis from DMM and o-xylene using a synthetic acidic aluminosilicate (Zeolithe Catalyst H Beta 25) using an experimental set up similar to that described in Comparative Example 2.

The results of this trial can be seen in Table 2.

TABLE 2

| | Molar yield [%] using the catalyst: | | |
|---|---|---|---|
| Temperature | sulfonic acid resin (Amberlyst® XN 1010) (Comparative Example 2) | synthetic acidic aluminosilicate (Zeolithe Catalyst H Beta 25) (Comparative Example 3) | solid-supported perfluorosulfonic acid resin (Nafion® SAC-13) (Example 1) |
| 80 | 3 | — | 40 |
| 100 | 12 | — | 61 |
| 110 | 28 | — | — |
| 120 | 29 | 0 | 64 |
| 130 | 24 | 0 | 77 |
| 140 | 29 | 4 | 84 |
| 150 | 36-39[1] | 9 | 84 |
| 160 | — | 13 | 85 |
| 170 | — | 20 | 79 |
| 180 | — | 22 | 81-87 |
| 190 | — | 30-40[1] | |

[1]Decreased over time due to catalyst poisoning.
"—" means that no measurement was made under those listed conditions.
"0" means that a measurement was made but that the product, if present, was below the limit of detection of the analytical method.

Examples 4-5 and Comparative Examples 4-7

A tubular reactor (2.54 cm×38.1 cm stainless steel) was charged with 18.01 grams of the catalyst. The catalyst bed was dried by heating to 150° C. with a nitrogen purge overnight. The packed reactor was cooled to ambient temperature and a back pressure regulator, set to 1379 kPa, was attached to the exit of the reactor. The system was primed with o-xylene at 1 ml/min flow and the reactor bed was heated to 170° C. Once the reactor bed was at temperature, the pure o-xylene feed was replaced with a solution of 6% by weight DMM in o-xylene and the flow rate was maintained at 1 ml/min. The results of this trial can be seen in Table 3.

TABLE 3

| Example | Catalyst | Maximum molar yield [%] | Selectivity [%] | Conversion of DMM [%] | Temperature [° C.] |
|---|---|---|---|---|---|
| 4 | Solid supported perfluorosulfonic acid resin (Nafion® SAC 13) | 85 | 75 | 100 | 180 |
| 5 | Perfluorosulfonic acid resin | 60 | 70 | 100 | 160-180 |
| CE 4 | Synthetic acidic aluminosilicate (Zeolite Catalyst H Beta 25)[2] | 58 | 81 | 100 | 190 |

TABLE 3-continued

| Example | Catalyst | Maximum molar yield [%] | Selectivity [%] | Conversion of DMM [%] | Temperature [° C.] |
|---|---|---|---|---|---|
| CE 5 | Sulfonic acid resin (Amberlyst ® XN 1010)[3)] | 40 | 60 | 100 | 150 |
| CE 6 | Weakly acidic alumina | 0 | 0 | 0 | 140-340 |
| CE 7 | Neutral alumina pre-treated with polyphosphoric acid | 0 | 0 | 0 | 140-340 |

[2)]Catalyst can be regenerated by heating at 500° C.
[3)]Catalyst quality degenerated at 150° C.

The results of these examples and comparative examples show that the molar yield, the selectivity and the conversion rate of DMM have the highest values using a solid supported perfluorosulfonic acid resin.

It is the intent of the inventors herein that the description of any range shall be construed as the description of each value and all possible sub-ranges within the range and the description of any genus shall be construed as the description of each species and all possible sub-genuses within the genus.

Obviously, numerous modifications and variations of the present invention are possible in light of the above teachings. It is therefore to be understood that within the scope of the appended claims, the invention may be practiced otherwise than as specifically described herein.

The invention claimed is:

1. A process of producing a 1,1-diaryl alkane comprising condensing an aromatic compound having at least one aromatic hydrogen with an acetal, in the presence of a perfluorinated sulfonic acid in polymeric form as catalyst.

2. The process of claim 1, wherein the catalyst is a solid or supported acid.

3. The process of claim 2, wherein the catalyst is a supported perfluorinated sulfonic acid in polymeric form with silica as support material.

4. The process of claim 1, wherein the ratio of the acetal to the aromatic compound is from 4 to 10% by weight based on the aromatic compound.

5. The process of claim 4, wherein the ratio of the acetal to the aromatic compound is from 5 to 8% by weight based on the aromatic compound.

6. The process of claim 1, wherein the pressure during the condensation is from 1000 to 2000 kPa.

7. The process of claim 6, wherein the pressure during the condensation is from 1250 to 1500 kPa.

* * * * *